(12) United States Patent
Bektesevic et al.

(10) Patent No.: US 7,723,552 B2
(45) Date of Patent: May 25, 2010

(54) PROCESS FOR MAKING CHLOROTRIFLUOROETHYLENE FROM 1,1,2-TRICHLOROTRIFLUOROETHANE

(75) Inventors: Selma Bektesevic, Williamsville, NY (US); Michael John Murphy, Kenmore, NY (US)

(73) Assignee: Honeywell International Inc., Morristown, NJ (US)

(*) Notice: Subject to any disclaimer, the term of this patent is extended or adjusted under 35 U.S.C. 154(b) by 0 days.

(21) Appl. No.: 12/537,805

(22) Filed: Aug. 7, 2009

(65) Prior Publication Data

US 2010/0036178 A1    Feb. 11, 2010

Related U.S. Application Data

(60) Provisional application No. 61/087,482, filed on Aug. 8, 2008.

(51) Int. Cl.
*C07C 17/23* (2006.01)
*C07C 17/34* (2006.01)

(52) U.S. Cl. ...................... 570/155; 570/158
(58) Field of Classification Search ............... 570/155, 570/158
See application file for complete search history.

(56) References Cited

U.S. PATENT DOCUMENTS

| | | | | |
|---|---|---|---|---|
| 2,754,336 A | * | 7/1956 | Chernosky et al. | 570/158 |
| 5,124,494 A | * | 6/1992 | Ishihara et al. | 570/158 |
| 7,164,050 B2 | * | 1/2007 | Cottrell et al. | 570/158 |

* cited by examiner

*Primary Examiner*—Sikarl A Witherspoon
(74) *Attorney, Agent, or Firm*—Bruce Bradford

(57) ABSTRACT

A process for the making chlorotrifluoroethylene. The process has the step of reacting 1,1,2-trichlorotrifluoroethane with a reducing metal in the presence of a polar aprotic solvent under conditions sufficient to form chlorotrifluoroethylene.

18 Claims, No Drawings

PROCESS FOR MAKING CHLOROTRIFLUOROETHYLENE FROM 1,1,2-TRICHLOROTRIFLUOROETHANE

CROSS-REFERENCE TO A RELATED APPLICATION

The present application claims priority based on U.S. Provisional Application No. 61/087,482, filed Aug. 8, 2008, which is incorporated herein it its entirety.

BACKGROUND OF THE INVENTION

1. Field of the Invention

The present invention relates to a process for the making chlorotrifluoroethylene (CFO-1113) from 1,1,2-trichlorotrifluoroethane (CFC-113).

2. Description of the Related Art

Chlorotrifluoroethylene (CFO-1113) is currently manufactured commercially by dechlorinating 1,1,2-trichlorotrifluoroethane (CFC-113) via reaction with zinc in the presence of methanol as a solvent. A major drawback with this process is the formation of 1,2-dichloro-1,1,2-trifluoroethane (HCFC-123a) as a major byproduct, which greatly reduces the yield of CFO-1113 and is costly to dispose of.

It would be desirable to have an improved process for making CFO-1113 from CFC-113.

SUMMARY OF THE INVENTION

According to the present invention, there is provided a process for the making chlorotrifluoroethylene. The method has the step of reacting 1,1,2-trichlorotrifluoroethane with a reducing metal in the presence of one or more polar aprotic solvents under conditions sufficient to form chlorotrifluoroethylene.

DETAILED DESCRIPTION OF THE INVENTION

The process of the present invention has the following reaction sequence:

$$CFCl_2-CF_2Cl + M \longrightarrow CF_2=CFCl + MCl_x$$

(CFC—113)   (CFO—1113 + metal chloride)

wherein M is a reducing metal and wherein the reaction (dechlorination) is carried out in the presence of a polar aprotic solvent. When M is zinc, the reaction sequence is the following:

$$CFCl_2-CF_2Cl + Zn \longrightarrow CF_2=CFCl + ZnCl_2$$

(CFC—113)   (CFO—1113 + zinc chloride)

Polar aprotic solvents are solvents that have similar dissolving power to protic solvents, but without the presence of an acidic hydrogen. Useful polar aprotic solvents include, but are not limited to, aldehydes (R—CHO), ketones (R—CO—R'), dimethyl sulfoxide (DMSO) ($CH_3$—SO—$CH_3$), dimethyl formamide (DMF) (H—CO—N($CH_3$)$_2$), and combinations thereof wherein R and R' are alkyl groups having 1 to about 4 carbon atoms. Examples of useful polar aprotic solvents include ethyl ether, ethyl acetate, acetone, and methyl ethyl ketone. Aprotic solvents have the advantage of producing lower amounts of byproducts. More particularly, polar aprotic solvents have the advantage of producing lower amounts of none of the byproduct HCFC-123a. Although not bound by any particular theory, it is conjectured that protic solvents (e.g., methanol) cause the formation of HCFC-123a by losing an acidic hydrogen to a reaction intermediate. Use of polar aprotic solvents will reduce or eliminate the formation of hydrogen-containing byproducts.

Useful polar aprotic solvents are those capable of dissolving the reactant and the reaction products, i.e., CFC-113, CFO-1113 and $MCl_x$ (chloride of the reducing metal). A polar aprotic solvent is preferably used in an amount sufficient to substantially dissolve the reactant and the reaction products.

The solvent system may be made up substantially or entirely of a polar aprotic solvent(s) or combinations of a polar aprotic solvent(s) and a protic solvent(s). In the instance of combinations, the amount of protic co-solvent can range from about 1 wt. % to about 80 wt. % and more preferably about 5 wt. % to about 40 wt. % based on the total weight of the polar aprotic solvent(s) and the protic co-solvent(s).

Protic co-solvents useful in combination with the aprotic solvents include methanol, ethanol, propanol, isopropanol, and water.

Useful examples of useful reducing metals include zinc, magnesium, aluminum, and tin. A preferred reducing metal is zinc.

The dechlorination reaction is carried out under conditions sufficient to form chlorotrifluoroethylene. The reaction is preferably carried out at a temperature of about 50° C. to about 100° C., more preferably about 60° C. to about 90° C., and most preferably about 60° C. to about 85° C. The reaction can be carried under vacuum, atmospheric, or superatmospheric pressure conditions. The reaction vessel is preferably an agitated pressure vessel. The process can be either batch or continuous.

The following are examples of the present invention, and are not to be construed as limiting.

EXAMPLES

Examples of the process of the invention and a comparative example were tested for conversion.

Comparative Example

In a plant operation test, only a protic solvent, MeOH, was used. Starting materials of 1.08 liters of methanol and 0.32 kilogram of zinc per kilogram of CFC-113 were charged into a batch reactor equipped with agitation. The reaction was carried out at ~73° C. The conversion of CFC-113 and selectivity to CFO-1113 were 92.4% and 94.1%, respectively.

Example 1

This is an example that demonstrates using only an aprotic solvent.

65 grams of zinc powder was charged into a one-liter agitated pressure vessel. The vessel was then sealed, pressure checked, and evacuated. Approximately 175-250 milliliters of acetone were charged into the reactor on top of the zinc followed by an addition of 200 grams of CFC-113. The vessel was heated to a temperature necessary to run the reaction, approximately 60° C.-85° C. with agitation. The reaction was run for 220 minutes after the temperature was stabilized at the desired setting. During the reaction, the pressure rose to 150 psig. After the run was completed, the volatile reaction products were transferred to a chilled and evacuated product collection cylinder by venting the pressure from the reactor down to atmospheric. The collected material was analyzed using Gas Chromatography (GC) which revealed that conversion of CFC-113 was 88.6%, while selectivity to CFO-1113 was 99.8%.

Example 2

The process of Example 2 was run substantially as described in Example 1 except that a mixture of acetone and methanol (80:20) was used as the solvent instead of acetone alone. Conversion of CFC-113 and selectivity to CFO-1113 were 99.4% and 99.6%, respectively. The presence of methanol had the effect of increasing conversion and the presence of the polar aprotic solvent, acetone, improved selectivity to CFO-1113.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A process for the making chlorotrifluoroethylene, comprising reacting 1,1,2-trichlorotrifluoroethane with a reducing metal in the presence of one or more polar aprotic solvents and one or more protic co-solvents under conditions sufficient to form chlorotrifluoroethylene.

2. The process of claim 1, wherein the mixture has about 1 wt. % to about 80 wt. % of the one or more protic solvents based on the total weight of the mixture of the one or more polar aprotic solvents and the one or more protic co-solvents.

3. The process of claim 1, wherein the mixture has about 5 wt. % to about 40 wt. % of the one or more protic solvents based on the total weight of the aprotic solvent(s) and the protic co-solvent(s).

4. The process of claim 1, wherein the one or more polar aprotic solvents is selected from the group consisting of aldehydes, ketones, dimethyl sulfoxide, dimethyl formamide, and combinations thereof.

5. The process of claim 1, wherein the one or more polar aprotic solvents is selected from the group consisting of ethyl ether, ethyl acetate, acetone, methyl ethyl ketone, and combinations thereof.

6. The process of claim 1, wherein the polar aprotic solvent is ethyl acetate.

7. The process of claim 1, wherein the polar aprotic solvent is acetone.

8. The process of claim 1, wherein the polar aprotic solvent is methyl ethyl ketone.

9. The process of claim 1, wherein the polar aprotic solvent is ethyl ether.

10. The process of claim 1, wherein the protic solvent is selected from the group consisting of methanol, ethanol, propanol, isopropanol, and water.

11. The process of claim 10, wherein the protic solvent is water.

12. The process of claim 1, wherein the reducing metal is selected from the group consisting of zinc, magnesium, aluminum, and tin.

13. The process of claim 1, wherein the reducing metal is zinc.

14. The process of claim 1, wherein the reaction is carried out at a temperature of about 50° C. to about 100° C.

15. The process of claim 1, wherein the reaction is carried out at a temperature of about 60° C. to about 90° C.

16. The process of claim 1, wherein the reaction is most preferably carried out at a temperature of about 60° C. to about 85° C.

17. The process of claim 1, wherein the reaction is carried out in batch.

18. The process of claim 1, wherein the mixture has about 5 wt. % to about 40 wt. % of the one or more protic solvents based on the total weight of the aprotic solvent(s) and the protic co-solvent(s), wherein the one or more polar aprotic solvents is selected from the group consisting of ethyl ether, ethyl acetate, acetone, methyl ethyl ketone, and combinations thereof, wherein the protic solvent is selected from the group consisting of methanol, ethanol, propanol, isopropanol, and water wherein the reducing metal is selected from the group consisting of zinc, magnesium, aluminum, and tin, and wherein the reaction is carried out at a temperature of about 50° C. to about 100° C.

* * * * *